United States Patent [19]

Iwasaki et al.

[11] Patent Number: 4,844,734

[45] Date of Patent: Jul. 4, 1989

[54] PROCESS FOR THE PREPARATION OF GRANULAR PESTICIDE

[75] Inventors: Tetsuji Iwasaki; Takuo Goto, both of Wakayama; Tadao Matsumoto, Osaka, all of Japan

[73] Assignee: Kao Corporation, Tokyo, Japan

[21] Appl. No.: 56,507

[22] Filed: May 29, 1987

[30] Foreign Application Priority Data

Jul. 14, 1986 [JP] Japan .................. 61-165301

[51] Int. Cl.$^4$ .................. A01N 47/30
[52] U.S. Cl. .................. 71/120; 71/DIG. 1; 71/118; 71/94; 71/98; 71/86; 514/785; 514/786; 514/567; 514/143; 514/483
[58] Field of Search .................. 71/120; 526/124; 525/268

[56] References Cited

U.S. PATENT DOCUMENTS

| | | | |
|---|---|---|---|
| 2,768,971 | 10/1956 | Jones | 564/53 |
| 3,951,641 | 4/1976 | Janiok | 71/120 |
| 4,460,700 | 7/1984 | Candlin et al. | 526/124 |
| 4,602,021 | 7/1986 | Kristiansen | 514/336 |

*Primary Examiner*—Glennon H. Hollrah
*Assistant Examiner*—Amelia A. Owens
*Attorney, Agent, or Firm*—Flynn, Thiel, Boutell & Tanis

[57] ABSTRACT

A granular pesticide containing a surfactant as a synergist can be prepared by countercurrent spray drying under specified conditions. The obtained granular pesticide exhibits excellent fluidity and storage stability and is excellent in wettability and disintegratability.

10 Claims, No Drawings

PROCESS FOR THE PREPARATION OF GRANULAR PESTICIDE

BACKGROUND OF THE INVENTION

1. Field of the Invention

The present invention relates to a process for the preparation of a granular pesticide. Particularly, it relates to a process for the preparation of a granular pesticide containing a synergist.

2. Description of the Prior Art

Various pesticides such as insecticides, bactericides, herbicides, acaricides or plant growth regulators are now used as emulsions, wettable powders, flowable powders, granules, soluble powder or the like. Among them, wettable powders and soluble powders are advantageous in terms of storage stability, cost, environmental pollution and damage to crops due to drug-induced suffering.

In the meantime, the addition of a synergist selected from among various surfactants to a pesticide has been examined in order to sufficiently bring out the activity of the latter. Under existing circumstances, where the development of novel pesticides is becoming more and more difficult, it has become important to enhance the activity of known pesticides.

However, not satisfactory wettable and soluble pesticide powders containing a synergist selected from among various surfactants can be prepared by a process using an ordinary granulator or by the cocurrent spray drying. More precisely, it has been confirmed that the former process causes frothing during granulation and gives a sticky product, while the latter process gives a product which is poor in disintegratability, solubility or wettability and causes dusting.

The inventors of the present invention have made extensive studies with the purpose of overcoming the above problems and have found that the purpose can be attained by subjecting a concentrated aqueous solution or slurry of a pesticide containing a synergist selected from among various surfactants to countercurrent spray drying under specified conditions. The present invention has been accomplished on the basis of this finding.

SUMMARY OF THE INVENTION

The present invention provides a process for the preparation of a granular pesticide which comprises subjecting a concentrated aqueous solution or slurry containing (a) a pesticide and (b) at least one surfactant selected from the group consisting of (b-1) quaternary ammonium salt cationic surfactants and (b-2) betaine, organic amino acid, amine oxide and imidazoline amphoteric surfactants at a weight ratio of (a) to (b) of between 1:0.5 and 1: ; 20 to countercurrent spray drying under the conditions comprising a diameter of a spray nozzle of 0.5 to 4.0 mm, a spray pressure of 5 to 250 $kg/cm^2$ (pressure nozzle), an inlet temperature of hot gas of 150° to 300° C. and an exhaust temperature of 60° to 120° C.

DETAILED DESCRIPTION OF PREFERRED EMBODIMENTS

Examples of the quaternary ammonium salt cationic surfactant (b-1) to be used in the present invention include the following compounds:

alkyl - or alkenyl-trimethylammonium chloride wherein the alkyl and alkenyl groups may be each straight-chain or branched and each have 8 to 22 carbon atoms, dialkyl- or dialkenyl-dimethylammonium chloride wherein the alkyl and alkenyl groups may be each straight-chain or branched and each have 8 to 22 carbon atoms, dialkyl- or dialkenyl-dipolyoxyalkyleneammonium bromide wherein the alkyl and alkenyl groups may be each straight-chain or branched and each have 8 to 22 carbon atoms, N-alkylaminoethyl-N,N-dimethyl-N-hydroxyethylammonium chloride wherein the alkyl group may be straight-chain or branched and has 8 to 22 carbon atoms, alkyldimethylbenzylammonium chloride wherein the alkyl group may be straight-chain or branched and has 8 to 22 carbon atoms, and alkyloylpropyl-N,N-dimethyl-N-benzylammonium chloride wherein the alkyloyl group may be straight-chain or branched and has 8 to 22 carbon atoms.

Examples of the amphoteric surfactant (b-2) to be used in the present invention include the following compounds:

(1) betaines such as alkyl- or alkenyl-dimethyl betaine wherein the alkyl and alkenyl groups may be each straight-chain or branched and each have 8 to 22 carbon atoms, N-alkyloidaminoethyl-N-hydroxyethyl-N,N-dicarboxymethylammonium betaine wherein the alkyloid group may be straight-chain or branched and has 8 to 22 carbon atoms, N-alkyloidaminoethyl-N,N-dimethyl-N-sulfoethylammonium betaine wherein the alkyloid group may be straight-chain or branched and has 8 to 22 carbon atoms, and N,N,N-trialkyl-N-sulfoethylpolyoxyethyleneammonium betaine wherein the alkyl groups may be each straight-chain or branched and each have 8 to 22 carbon atoms, (2) organic amino acids such as N-β-hydroxyalkyl- or alkenyl-imino-N,N-bisethoxyacetic acid and salts thereof wherein the alkyl and alkenyl groups may be each straight-chained or branched and each have 8 to 22 carbon atoms, salts of N-β-hydroxyalkyl- or alkenyl-glycine wherein the alkyl and alkenyl groups may be each straight-chain or branched and each have 6 to 22 carbon atoms, salts of N-β-hydroxyalkyl- or alkenyl-iminodiacetic acid wherein the alkyl and alkenyl groups may be each straight-chain or branched and each have 6 to 22 carbon atoms, and salts of N-alkyl- or alkenyl-N,N-dipolyoxyalxylene disulfate wherein the alkyl and alkenyl groups may be each straight-chain or branched and each have 6 to 22 carbon atoms, (3) amine oxides such as alkyl- or alkenyl-dimethylamine oxide wherein the alkyl and alkenyl groups may be each straight-chain or branched and each have 8 to 22 carbon atoms, and alkyl- or alkenyl-diethylene oxide amine oxide wherein the alkyl and alkenyl groups may be each straight-chain or branched and each have 8 to 22 carbon atoms, and (4) imidazolines such as
2-alkyl- or alkenyl-N-carboxymethyl-N-hydroxyethylimidazolinium betaine wherein the alkyl and alkenyl groups may be each straight-chain or branched and each have 8 to 18 carbon atoms, and 2-alkyl- or alkenyl-imidazolylpolyoxethylenesuflonic acid and salts thereof wherein the alkyl and alkenyl groups may be each straight-chain or branched and each have 6 to 22 carbon atoms.

Further, when both the cationic surfactant (b-1) and the amphoteric surfactant (b-2) are added to a pesticide, the biological effect of the pesticide is further enhanced. In this case, the ratio of the surfactant (b-1) to the surfactant (b-2) is preferably between 1:0.2 and 0.2:1.

The pesticide to be applied in the present invention are as follows:

Insecticides: pyrethroid insecticides such as fenvalerate ($\alpha$-cyano-3-phenoxybenzyl 2-(4-chlorophenyl)-3-methylvalerate) or Bayth-roid (cyano(4-fluoro-3-phenoxyphenylmethyl-3-(2,2-dichloroethenyl)-2,2-dimethylchloropropanecarboxylate); organophosphorus insecticide such as DDVP (2,2-dichlorovinyl dimethyl phosphate), Sumithion (dimethyl 4-nitro-m-tolyl phosphorothionate), Malathon (S-[1,2-bis(ethoxycarbonyl)ethyl] dimethyl phosphorothiolothionate), dimethoate (dimethyl S-(N-methylcarbamoylmethyl) phosphorothiolothionate), Elsan (S-[$\alpha$-(ethyoxycarbonyl)benzyl] dimethyl phosphorothiolothionate) or Baycid (0,0-dimethyl O-(3-methyl-4-methylmercaptophenyl)thiophosphate)); carbamate insectisides such as Bassa (O-butylphenyl methyl carbamate), MTMC(m-tolyl methylcarbamate), Meobal (3,4-dimethylphenyl N-methylcarbamate), NAC(1-napthyl N-methylcarbamate); other insectisides such as methomyl(methyl N-[(methylcarbamoyl)oxy] thioacetiamidate) or Cartap (1,3-bis(carbamoylthio)-2-(N,N-dimethylamino)propane hydrochloride).

Acaricides: Smite (2-[2-(p-t-butylphenoxy)-isopropoxy]-isopropyl 2-chloroethyl sulfide), Acricid (2,4-dinitro-6-sec-butylphenyl dimethylacrylate), chlormite(isopropyl 4,4-dichlorobenzilate), Akar(ethyl 4,4-dichlorobenzilate), Kelthane(1,1-bis(p-chlorophenyl)-2,2,2-trichloroethanol), Citrazon(ethyl O-benzoyl-3-chloro-2,6-dimethoxybenzohydroxamate), Plictran(-tricyclohexyltin hydroxide) or Omite(2-(p-tert-butylphenoxy)cyclohexyl 2-propynyl sulfite).

Bactericides:organosulfur bactericide such as Dithane (zinc ethylenebisdithiocarbamate), Maneb(manganese ethylenebisdithiocarbamate) or thiram(bis(dimethylthiocarbamoyl) disulfide); other bactericide such as Benlate(methyl 1-(butylcarbamonyl)-2-benzimidazolecarbamate), Defoltan(N-tetrachloroethylthio-4-cyclohexone-1,2-dicarboximide), Daconil(tetrachloroisophthalonitrile), Pansoil(5-ethoxy-3-trichloromethyl-1,2,4-thiadiazole), thiophanate-methyl(1,2-bis(3-methoxycarbonyl-2-thioureido)benzene), Rabcide(4,5,6,7-tetrachlorophthalide), Kitazin-P (O,O-diisopropyl S-benzyl phosphorothioate), Hinosan-(O-ethyl S,S-diphenyl dithiophosphate) or Probenazole(3-allyloxyl-1,2-benzothiazole 1,1-dioxide).

Herbicides: Stam(3,4-dichloropropionanilide), Saturn(S-(4-chlorobenzyl) N,N-diethylthiolcarbamate), Lasso(2-chloro-2',6'-diethyl-N-(methoxymethyl-)acetanilide), DCMU(3-(3,4-dichlorophenyl)-1,1-dimethylurea) or Gramoxone(1,1'-dimethyl-4,4'-dipyridinium dichloride).

Plant growth regulators: MH (maleic hydrazide) or Ethrel(2-chloroethylphosphonic acid).

The concentration of the concentrated aqueous solution or slurry containing (a) the pesticide and (b) the cationic and/or amphoteric surfactant according to the present invention is generally 10 to 80 % by weight, preferably 30 to 70 % by weight.

When the granular pesticide is a wettable powder, a mineral powder can be added in an amount of at most 60 % by weight, preferably 2 to 50 % by weight based on the final product.

The mineral powder to be used in the present invention preferably has a particle size smaller than 300 mesh to thereby allow the easy preparation of granule having a recessed part which is the objective product according to the present invention. Examples of the mineral powder include pyrophyllite, talc, kaolin, calcium carbonate, bentonite, silica powder, limestone powder, acid clay, diatomaceous earth powder, gypsum, pumice powder, seashell powder, mica powder and colloidal hydrous sodium silicate.

When the granular pesticide is a wettable powder, a dispersant can be also added to the above concentrated slurry. The amount of the dispersant is at most 50 % by weight, preferably 4 to 40 % by weight based on the final product.

Examples of the dispersant to be used can be classified into the following three groups (1) to (3).

(1) Water-soluble or dispersible (co)polymer comprising one or more monomer selected from among unsaturated carboxylic acids and derivatives thereof as essential constituent(s).

Examples of the monomer to be used in the preparation of the above (co)polymer include unsaturated monocarboxylic acids, for example, acrylic acid and methacrylic acid; unsaturated dicarboxylic acids for example, maleic acid; derivatives thereof, for example, alkyl esters such as methyl ester, alkali metal salts such as sodium salt, ammonium salts and organic amine salts such as triethanolamine salt of these acids and mixtures thereof. Further, other monomers such as vinyl acetate, isobutylene, diisobutylene or styrene can be copolymerized with the above momoners.

The polymerization of the above monomers can be carried out by an ordinary process. Although neither the ratio of monomer components nor the degree of polymerization is particularly limited, the obtained polymer must be at least water-soluble or waterdispersible.

Examples of the (co)polymer include polyacrylic acid, polymethacrylic acid, acrylic acid-methacrylic acid copolymer acrylic acid-methyl acrylate copolymer, acrylic acid-vinyl acetate polymer, acrylic acid-maleic acid copolymer, maleic acid-isobutylene copolymer, maleic acid-styrene copolymer and salts thereof with alkali metal, ammonium or organic amine. Two or more polymers selected from among these polymers can be used.

(2) Water-soluble or dispersible (co)polymers comprising styrenesulfonic acid salt as an essential constituent.

The homopolymer of styrenesulfonic acid salt can be easily prepared by polymerizing a styrenesulfonic acid salt or by sulfonating polystyrene. The homopolymer has a skeleton represented by the formula:

$$-(\text{CH}_2-\text{CH})_n-$$
$$\underset{\text{SO}_3\text{M}}{\bigcirc}$$

The polymer has a molecular weight of at least 1,000, preferably 10,000 to 3,000,000. M stands for an alkali metal such as Li, Na or K, $NH_3$, an alkylamine or an alkanolamine.

The copolymer of a styrenesulfonic acids salt with other monomer can be easily prepared by copolymerizing a styrenesulfonic acid salt with other monomer or by sulfonating a copolymer of styrne with other monomer. Examples of the monomer to be copolymerized with a styrenesulfonic acid salt include hydrophobic monomers such as alkyl acrylate, alkyl methacrylate, vinyl alkyl ether, vinyl acetate, ethylene, propylene, butylene, butadiene diisobutylene, vinyl chloride, vinylidene chloride, acrylonitrile and styrene and hydrophilic monomers such as acrylic acid, methacrylic acid, maleic acid, fumaric acid, maleic anhydride, vinyl alcohol, acrylamide, methacrylamide, diacetone acrylamide, N-vinylpyrrolidone, 2-acrylamide-2-methylpropanesulfonic acid and methallylsulfonic acid. Preferred examples of the salt of the copolymer include those of (meth) acrylic acid-styrenesulfonic acid copolymers. The molar ratio of (meth)acrylic acid to styrenesulfonic acid of the copolymer is between 1:10 and 10:1, preferably between 1:3 and 7:1. The average molecular weight thereof is 1,000 to 1,000,000, preferably 10,000 to 700,000. Examples of the salt of the copolymer include salts thereof with sodium, potassium, ammonium, diethanolamine, triethanolamine, monoisopropanolamine, diisopropanolamine, triisopropanolamine or 2-amino-2-methyl-propane-1, 3-diol. Further, the salt of the copolymer may contain an unneutralized moiety to such an extent as not to arrest the performance.

(3) Condensate of sulfonated aromatic compound optionally having a hydrocarbyl substituent with formalin and salts thereof.

Examples of the condensate include those of formalin with petroleumsulfonic acid derivatives, lignosulfonic acid derivatives, naphthalenesulfonic acid derivatives and alkylbenzenesulfonic acid derivatives.

These condensates can be preared by sulfonating naphthalene, alkyl-substitued benzene, alkylsubstituted naphthalene, anthracene, alkylsubstituted anthracene, lignin or aromatic compounds contained in petroleum residue, converting the sulfonation product into the corresponding salt and condensing the salt with formalin. The degree of condensation is preferably 2 to 30, still preferably 3 to 10. If the degree of condensation is less than 2, the condensation effect will be hardly attained, while if it exceeds 30, the resulting condensate will have too high a molecular weight to give sufficiently high solubility, thus being problematic in practical use.

Although various aromatic compounds can be used, preferred examples of the aromatic compounds include lignin, xylene, toluene, naphthalene and $C_{1\sim 6}$ alkyl-substituted naphthalene. Of course, a mixture thereof can be used.

Examples of the salt of the condensate include salts thereof with an alkali metal such as sodium or potassium, an alkaline earth metal such as calcium, an amine and ammonium.

The most important requirement of the present invention is to carry out the spray drying of the pesticide in a countercurrent system. Further, other requirements such as the a diameter of the spray nozzle, spray pressure, inlet temperature of hot gas and exhaust temperature are also important.

The diameter of a spray nozzle is 0.5 to 4.0 mm, preferably 0.6 to 3,8 mm, while the spray pressure is 5 to 250 $kg/cm^2$, preferably 6 to 180 $kg/cm^2$. The inlet temperature of hot gas is 150° to 300° C., preferably 170° to 280° C., while the exhaust temperature is 60° to 120° C., preferably 70° to 100° C.

According to the present invention, with the purpose of further enhancing the biological effect of a pesticide, one or more polyoxyalkylene nonionic surfactants can be added. In this case, the weight ratio of the pesticide (a) to the polyoxyalkylene nonionic surfactant (c) is preferably between 1:0.1 and 1:20, still preferably between 1:0.5 and 1:10.

The present invention will be further described in more detail together with the function and effect thereof.

A spray tower fitted with an inlet for feeding hot gas in the lower part, an outlet for exhaust gas in the upper part or at the top and spray nozzles each having a diameter of 0.5 to 4.0 mm for spraying fluid into the tower in the upper part or at the top is used. Hot gas is fed to the tower upward from the inlet to form an ascending flow of hot gas in the tower. The gas is with drawn from the outlet. A concentrated aqueous solution or slurry containing (a) the pesticide and (b) the surfactant and, if necessary, (c) the polyoxyalkylene nonionic surfactant which is optionally added depending upon the kind of the pesticide formulation to be prepared at a weight ratio of (a) to (b) of between 1:0.5 and 1:20 is sprayed downward into the tower under a pressure at a nozzle inlet of 5 to 250 $kg/cm^2$ to form many fine droplets. The droplets fall slowly through the ascending flow of hot gas and are heated by the hot gas to lose a part of the water contained therein by evaporation, thus forming shrunk droplets having dry surfaces. The shrunk droplets are further heated, thus also losing the remaining water, so that nearly hollow and dry granules each having a size larger than that of the initial droplet are formed. The granules are taken out of the bottom of the tower. In this spray drying process, the feed rate of hot gas and the spray rate of the aqueous solution or slurry must be so controlled as to keep the inlet temperature of hot gas at 150° to 300° C. and the exhaust temperature thereof at 60° to 120° C.

The gas to be used in the present invention may be any inert gas such as air, nitrogen or carbon dioxide. Further, it may be combustion gas.

The granular pesticide prepared by the present invention exhibits good fluidity and storage stability and is excellent in wettability and disintegratability.

The present invention will be further described in detail by the following Formulatin Examples, Examples and Experimental Examples.

| Formulation Example 1 (Preparation of slurry) | |
|---|---|
| 3-(3,4-dichlorophenyl)-1,1-dimethylurea | 40 parts by weight |
| stearyltrimethylammonium chloride | 30 parts by weight |

-continued

| Formulation Example 1 (Preparation of slurry) | |
|---|---|
| sodium lignosulfonate | 0.5 parts by weight |
| clay | 29.5 parts by weight |

The above components were dissolved and/or dispersed in 100 parts by weight of water to obtain a homogeneous slurry.

| Formulation Example 2 (Preparation of slurry) | |
|---|---|
| 1,1'-dimethyl-4,4'-dipyridium dichloride | 30 parts by weight |
| didecyldipolyoxyethylene(2 mol)ammonium chloride | 30 parts by weight |
| Glauber's salt | 40 parts by weight |

The above components were dissolved in 70 parts by weight of water to obtain a slurry.

| Formulation Example 3 (Preparation of slurry) | |
|---|---|
| 2-chloroethylphosphonic acid | 20 parts by weight |
| lauryldimethylbenzylammonium chloride | 20 parts by weight |
| lauryldimethylbetaine | 20 parts by weight |
| Glauber's salt | 40 parts by weight |

The above components were dissolved in 50 parts by weight of water to obtain a slurry.

| Formulation Example 4 (Preparation of slurry) | |
|---|---|
| zinc ethylenebisdithiocarbamate | 50 parts by weight |
| lauryldimethylamine oxide | 25 parts by weight |
| polysodium styrenesulfonate (MW: 20,000) | 1 parts by weight |
| bentonite | 24 parts by weight |

The above components were dissolved in 70 parts of water to obtain a slurry.

| Formulation Example 5 (Preparation of slurry) | |
|---|---|
| dimethyl 4-nitro-m-tolyl phosphonothioate | 30 parts by weight |
| distearyldimethylammonium chloride | 15 parts by weight |
| sodium N—β-hydroxystearyliminodiacetate | 15 parts by weight |
| sodium styrenesulfonate-styrene copolymer (1/1 MW:30,000) | 0.5 parts by weight |
| clay | 39.5 parts by weight |

The above components were dissolved in 120 parts by weight of water to obtain a slurry.

| Formulation Example 6 (Preparation of slurry) | |
|---|---|
| tetrachloroisophthalonitrile | 30 parts by weight |
| 2-lauryl-N—carboxymethyl-N—hydroxyethylimidazolinium betaine | 20 parts by weight |
| sodium butylnaphthalenesulfonate | 0.5 parts by weight |
| clay | 49.5 parts by weight |

The above components were dissolved in 100 parts by weight of water to obtain a slurry.

| Formulation Example 7 (Preparation of slurry) | |
|---|---|
| α,α,α-trifluoro-2,6-dinitro-N,N—dipropyl-p-toluidine | 30 parts by weight |
| sodium N—β-hydroxylaurylglycinate | 25 parts by weight |
| naphthalenesulfonic acid-formalin condensate | 0.5 parts by weight |
| clay | 44.5 parts by weight |

The above components were dissolved in 100 parts by weight of water to obtain a slurry.

| Comparative Formulation Example 1 (Preparation of comparative slurry) | |
|---|---|
| 3-(3,4-dichlorophenyl)-1,1-dimethylurea | 40 parts by weight |
| sodium lignosulfonate (dispersant) | 0.5 parts by weight |
| clay | 59.5 parts by weight |

The above components were dispersed in 100 parts by weight of water to obtain a homogeneous slurry.

| Comparative Formulation Example 2 (Preparation of comparative slurry) | |
|---|---|
| 1,1'-dimethyl-4,4'-dipyridinium dichloride | 30 parts by weight |
| Glauber's salt | 70 parts by weight |

The above components were dissolved in 70 parts by weight of water to obtain a slurry.

(Example of spray drying/Comparative Example of countercurrent spray drying)

EXAMPLE 1

The slurries prepared in Formulation Examples 1 to 7 and Comparative Formulation Examples 1 and 2 were each subjected to countercurrent spray drying by the use of a spray tower having a height of 16 m and an inside diamter of 4.5 m under the conditions comprising a spray pressure of 10 kg/cm$^2$, a diameter of a spray nozzle of 1.6 mm, an inlet temperature of hot gas of 200° C. and an exhaust temperature of 80° C.

EXAMPLE 2

The slurries prepared in Formulation Examples 1 to 7 and Comparative Formulation Examples 1 and 2 were each subjected to countercurrent spray drying under the conditions comprising a spray pressure of 100 kg/cm$^2$, a diameter of a spray nozzle of 2.8 mm, an inlet temperature of hot gas of 280° C. and an exhaust temperature of 120° C.

COMPARATIVE EXAMPLE 1

The slurries prepared in Formulation Examples 1 to 7 and Comparative Formulation Examples 1 and 2 were each subjected to counter-current spray drying under the conditions comprising a spray pressure of 100 kg/cm$^2$, a diameter of a spray nozzle of 0.2 mm, an inlet temperature of hot gas of 140° C. and an exhaust temperature of 50° C.

COMPARATIVE EXAMPLE 2

The slurries prepared in Formulation Examples 1 to 7 and Comparative Formulation Examples 1 and 2 were each subjected to countercurrent spray drying under the conditions comprising a spray pressure of 10 kg/cm$^2$, a diameter of a spray nozzle of 4.2 mm, an inlet temperature of hot gas of 280° C. and an exhaust temperature of 150° C. (Comparative Example of Cocurrent spray drying)

COMPARATIVE EXAMPLE 3

The slurries prepared in Formulation Examples 1 to 7 and Comparative Formulation Examples 1 and 2 were subjected to cocurrent spray drying under the conditions comprising a spray pressure of 15 kg/cm$^2$, a diameter of a spray nozzle of 1.2 mm, an inlet temperature of hot gas of 220° C. and an exhaust temperature of 100° C.

COMPARATIVE EXAMPLE 4

The slurries prepared in Formulation Examples 1 to 7 and Comparative Formulation Examples 1 and 2 were subjected to cocurrent spray drying under the conditions comprising a spray pressure of 100 kg/cm$^2$, a diameter of a spray nozzle of 3.0 mm, an inlet temperature of hot gas of 280° C. and an exhaust temperature of 110° C.

COMPARATIVE EXAMPLE 5

The slurries prepared in Formulation Examples 1 to 7 and Comparative Formulation Examples 1 and 2 were subjected to cocurrent spray drying under the conditions comprising a spray pressure of 1 kg/cm$^2$, a diameter of a spray nozzle of 0.3 mm, an inlet temperature of hot gas of 100° C. and an exhaust temperature of 50° C.

Experimental Example 1 (Evaluation of wettability)

0.5 g of the powder or granule prepared in each of the above Examples and Comparative Examples was gently thrown into a 300-ml wide-mouthed beaker containing 100 ml of hard water having a hardness of 3 (20° C.) from a height of 10 cm to determine the time required until the powder or granule was submerged.

The results are shown in Tables 1 to 4.

Experimental Example 2 (Evaluation of disintegratability)

0.5 g of the powder or granule prepared in each of the above Examples and Comparative Examples was thrown into a 250-ml cylinder fitted with a cap and containing 100 ml of hard water having a hardness of 3 (20° C.). The cylinder was gently tumbled to determine the frequency of tumbling required until the powder or granule was dispersed or dissolved. The disintegratability was evaluated according to the following criteria.

The results are shown in Tables 1 to 4.
Evaluation criteria
A: The powder or granule is disintegrated and dispersed and/or dissolved, just after thrown.
B: The powder or granule is disintegrated and dispersed and/or dissolved by tumbling 5 or less times.
C: The powder or granule is disintegrated and dispersed and/or dissolved by tumbling 10 or less times.
D: The powder or granule is disintegrated and dispersed and/or dissolved by tumbling 10 or more times.

Experimental Example 3 (Evaluation of particle size distribution)

The particle size distribution of the powder or granule prepared in each of the above Examples and Comparative Examples was measured by the use of an automatic particle size analyzer and evaluated according to the following criteria.

The results are shown in Tables 1 to 4.
Evaluation criteria

| | | |
|---|---|---|
| A: | the proportion of granules having a particle size of 150 μm or larger based on the whole granules 70% or above | |
| B: | the proportion of granules having a particle size of 150 μm or larger based on the whole granules 70% or above | 50 to 69% |
| C: | the proportion of granules having a particle size of 150 μm or larger based on the whole granules 70% or above | 30 to 49% |
| D: | the proportion of granules having a particle size of 150 μm or larger based on the whole granules 70% or above | 10 to 29% |
| E: | the proportion of granules having a particle size of 150 μm or larger based on the whole granules 70% or above | 9% or below |

Experimental Example 4 (Evaluation of dustiness)

The drift index of the powder or granule prepared in each of the above Examples and Comparative Examples was determined as follows:

10 g of the powder or granule prepared in each of the above Examples and Comparative Examples was spread downward into a 1 m$^3$ box by the use of a standard spreader. After allowing to stand for 5 minutes, particles suspending at a distance of 40 cm over the outlet of the spreader are absorbed by an absorption tube having an inside diameter of 27 cm and a height of 20 cm and containing 75 ml of water at a rate of 30 l/mm for 1 minute, collected therein and examined for transmittance at 610 nm. The value of "100 minus transmittance" is taken as drift index. The smaller this index, the lower the extent of drift.

The results are shown in Tables 1 to 4.

TABLE 1

| | | Experimental results (Example of counter-current spraying drying) | | | |
|---|---|---|---|---|---|
| Spray drying | Slurry | Exper. Ex. 1 wetta-bility (sec) | Exper. Ex. 2 disintegrat-ability (frequency) | Exper. Ex. 3 particle size distribu-tion | Exper. Ex. 4 dustiness |
| Ex. 1 | Formul. | | | | |
| | Ex. 1 | 5 | A | A | 5 |
| | Ex. 2 | 3 | A | A | 6 |
| | Ex. 3 | 5 | A | A | 5 |
| | Ex. 4 | 6 | A | A | 5 |
| | Ex. 5 | 2 | A | A | 10 |
| | Ex. 6 | 5 | A | A | 5 |
| | Ex. 7 | 3 | A | A | 7 |
| | Comp. Formul. | | | | |
| | Ex. 1 | 140 | D | D | 35 |
| | Ex. 2 | 260 | D | D | 38 |

TABLE 1-continued

Experimental results (Example of countercurrent spraying drying)

| Spray drying | Slurry | Exper. Ex. 1 wettability (sec) | Exper. Ex. 2 disintegratability (frequency) | Exper. Ex. 3 particle size distribution | Exper. Ex. 4 dustiness |
|---|---|---|---|---|---|
| Ex. 2 | Formul. | | | | |
| | Ex. 1 | 9 | A | A | 7 |
| | Ex. 2 | 10 | A | A | 8 |
| | Ex. 3 | 8 | A | A | 7 |
| | Ex. 4 | 10 | A | A | 9 |
| | Ex. 5 | 12 | A | A | 10 |
| | Ex. 6 | 10 | A | A | 10 |
| | Ex. 7 | 5 | A | A | 5 |
| | Comp. Formul. | | | | |
| | Ex. 1 | 360 | D | E | 35 |
| | Ex. 2 | 240 | D | E | 39 |

TABLE 2

Experimental results (Example of countercurrent spraying drying)

| Spray drying | Slurry | Exper. Ex. 1 wettability (sec) | Exper. Ex. 2 disintegratability (frequency) | Exper. Ex. 3 particle size distribution | Exper. Ex. 4 dustiness |
|---|---|---|---|---|---|
| Comp. Ex. 1 | Formul. | | | | |
| | Ex. 1 | 12 | B | D | 22 |
| | Ex. 2 | 9 | B | C | 27 |
| | Ex. 3 | 10 | B | C | 31 |
| | Ex. 4 | 13 | B | D | 19 |
| | Ex. 5 | 7 | B | D | 24 |
| | Ex. 6 | 10 | B | C | 26 |
| | Ex. 7 | 9 | B | C | 30 |
| | Comp. Formul. | | | | |
| | Ex. 1 | 140 | D | D | 78 |
| | Ex. 2 | 255 | D | D | 94 |
| Comp. Ex. 2 | Formul. | | | | |
| | Ex. 1 | 10 | C | A* | 0* |
| | Ex. 2 | 12 | C | A | 0 |
| | Ex. 3 | 9 | C | A | 0 |
| | Ex. 4 | 12 | C | A | 0 |
| | Ex. 5 | 12 | C | A | 0 |
| | Ex. 6 | 12 | C | A | 0 |
| | Ex. 7 | 7 | C | A | 0 |
| | Comp. Formul. | | | | |
| | Ex. 1 | 360 | D | A | 0 |
| | Ex. 2 | 245 | D | A | 0 |

Note:
*In Comparative Example 2, all samples gave coarse particles having a particle size of 150 μm or larger and substantially comprising undried paste, so that no good powder was obtained.

TABLE 3

Experimental results (Comparative Example of cocurrent spray drying)

| Spray drying | Slurry | Exper. Ex. 1 wettability (sec) | Exper. Ex. 2 disintegratability (frequency) | Exper. Ex. 3 particle size distribution | Exper. Ex. 4 dustiness |
|---|---|---|---|---|---|
| Comp. Ex. 3 | Formul. | | | | |
| | Ex. 1 | 10 | A | C | 24 |
| | Ex. 2 | 8 | A | C | 26 |
| | Ex. 3 | 9 | A | C | 30 |
| | Ex. 4 | 7 | A | C | 30 |
| | Ex. 5 | 10 | A | C | 20 |
| | Ex. 6 | 10 | A | C | 18 |
| | Ex. 7 | 10 | A | C | 20 |
| | Comp. Formul. | | | | |
| | Ex. 1 | 150 | D | E | 70 |
| | Ex. 2 | 290 | D | E | 64 |
| Comp. Ex. 4 | Formul. | | | | |
| | Ex. 1 | 15 | A | D | 26 |
| | Ex. 2 | 14 | A | D | 27 |
| | Ex. 3 | 10 | A | D | 32 |
| | Ex. 4 | 11 | A | D | 32 |
| | Ex. 5 | 10 | A | D | 25 |
| | Ex. 6 | 12 | A | D | 22 |
| | Ex. 7 | 15 | A | D | 24 |
| | Comp. Formul. | | | | |
| | Ex. 1 | 380 | D | E | 58 |
| | Ex. 2 | 220 | D | E | 55 |

TABLE 4

Experimental results (Comparative Example of cocurrent spray drying)

| Spray drying | Slurry | Exper. Ex. 1 wettability (sec) | Exper. Ex. 2 disintegratability (frequency) | Exper. Ex. 3 particle size distribution | Exper. Ex. 4 dustiness |
|---|---|---|---|---|---|
| Comp. Ex. 5 | Formul. | | | | |
| | Ex. 1 | 16 | C | D | 30 |
| | Ex. 2 | 15 | C | D | 35 |
| | Ex. 3 | 11 | C | D | 32 |
| | Ex. 4 | 12 | C | D | 32 |
| | Ex. 5 | 15 | C | D | 30 |
| | Ex. 6 | 15 | C | D | 34 |
| | Ex. 7 | 20 | C | D | 30 |
| | Comp. Formul. | | | | |
| | Ex. 1 | 380 | D | E | 60 |
| | Ex. 2 | 225 | D | E | 57 |

What is claimed is:

1. A process for the preparation of a granular agricultural pesticide comprising the steps of:
   (1) forming a concentrated aqueous mixture containing (a) a pesticide and (b) at least one surfactant selected from the group consisting of (b-1) quaternary ammonium salt cationic surfactants and (b-2) betaine, organic amino acid, amine oxide and imidazoline amphoteric surfactants, the weight ratio of (a) to (b) being between 1:0.5 and 1:20;
   (2) spraying said concentrated aqueous mixture in an upper part of a spray tower through spray nozzles having an orifice diameter of from 0.5 to 4.0 mm and a spray pressure of from 5 to 250 kg/cm$^2$;
   (3) introducing an inert gas at a temperature of from 150° to 300° C. into a lower part of said spray tower;
   (4) removing said inert gas at a temperature of from 60° to 120° C. from an upper part of said spray tower; and
   (5) removing said granular pesticide from a lower part of said spray tower.

2. The process of claim 1, wherein said inert gas is selected from the group consisting of air, nitrogen, carbon dioxide and combustion gas.

3. The process of claim 1, wherein the weight ratio of (a) to (b) is from 1:0.5 to 1:10.

4. The process of claim 1, wherein said inert gas is introduced into said spray tower at a temperature of 170° to 280° C.

5. The process of claim 1, wherein said inert gas is removed from said spray tower at a temperature from 70° to 100° C.

6. The process of claim 1, wherein said pesticide is 3-(3,4-dichlorophenyl)-1,1-dimethylurea.

7. The process of claim 2, wherein said surfactant is stearyltrimethylammonium chloride.

8. The process of claim 1, wherein the spray nozzle orifice diameter is 1.6 mm, the spray pressure is 10 kg/cm$^2$ and the inert gas is introduced in the spray tower at a temperature of 200° C. and removed at a temperature of 80° C.

9. The process of claim 1, wherein the spray nozzle orifice diameter is 2.8 mm, the spray pressure is 100 kg/cm$^2$ and the inert gas is introduced in the spray tower at a temperature 280° C. and removed at a temperature of 120° C.

10. The process of claim 1, wherein the spray nozzle orifice diameter is from 1.6 to 2.8 mm, the spray pressure is from 10 to 100 kg/cm$^2$ and the inert gas is introduced in the spray tower at a temperature of from 200° to 280° C. and removed at a temperature of from 80° to 120° C.

* * * * *

UNITED STATES PATENT AND TRADEMARK OFFICE
CERTIFICATE OF CORRECTION

PATENT NO. : 4 844 734
DATED : July 4, 1989
INVENTOR(S) : Tetsuji IWASAKI et al

It is certified that error appears in the above-identified patent and that said Letters Patent is hereby corrected as shown below:

Column 13, line 11; change "claim 2" to ---claim 1---.

Signed and Sealed this

Third Day of July, 1990

Attest:

HARRY F. MANBECK, JR.

*Attesting Officer*    *Commissioner of Patents and Trademarks*